United States Patent
Fisher et al.

(10) Patent No.: US 6,204,001 B1
(45) Date of Patent: Mar. 20, 2001

(54) METHODS FOR DETERMINING COMPOUNDS CAPABLE OF INHIBITING THE ACTIVITIES OF THE HA-RAS ONCONGENE

(75) Inventors: Paul B. Fisher, Scarsdale; Zao-Zhong Su, New York, both of NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/749,737

(22) Filed: Nov. 15, 1996

Related U.S. Application Data

(60) Provisional application No. 60/007,543, filed on Nov. 24, 1995.

(51) Int. Cl.$^7$ .................... G01N 33/574; G01N 33/573
(52) U.S. Cl. ..................... 435/7.23; 435/18; 435/23; 435/25
(58) Field of Search .................. 435/7.23, 18, 23, 435/25

(56) References Cited

PUBLICATIONS

Hiramatsu et al Cancer Letters (Sep. 30, 1993) vol. 73 Nos. 2–3, pp. 161–166.*
U.S. Patent No. 5,234,839 (McCormick et al.) issued Aug. 10, 1993 (attached here to as Exhibit 1).
U.S. Patent No. 5,470,970 (Sager et al.) issued Nov. 28, 1995 (attached hereto as Exhibit 2).
Contente S., et al., Expression of the gene rrg is associated with reversion of NIH 3T3 transformed LTR–c–H–ras (1990) Science 249: 796–798 (attached herto as Exhibit 4).
Gingras, et al., Transient alterations in the expression of protease and extracellular matrix genes during metastatic lung colonization by H–ras–transformed 10T$^{1/2}$ Fibroblasts (1990) Cancer Research 50: 4061–4066 (attached hereto as Exhibit 5).
Hajnal A., et al., Up–regulation of lysyl oxidase in spontaneous revertants of H–ras–transformed rat fibroblasts (1993)Cancer Res. 53: 4670–4675 (attached hereto as Exhibit 6).
Jiang, H., et al., Use of a sensitive and efficient subtraction hybridization protocol for the identification of genes differentially regulated during the induction of differentiation in human melanoma cells (1993) Mol. Cell. Different. 1: 285–299 (attached hereto as Exhibit 7).
Kagan H. M., et al., Properties and function of lysyl oxidase (1991) Am. J. Respir. Cell Mol. Biol. 5: 206–210 (attached hereto as Exhibit 8).
Kenyon K., et al., Lysyl oxidase and rrg messenger RNA (1990) Science 253: 802 (attached hereto as Exhibit 9).

Kenyon K., et al., A novel human cDNA with a predicted protein similar to lysyl oxidase maps to chromosome 15q24–q25 (1993) (attached hereto as Exhibit 10).
Kitayama, H., et al., A ras–related gene with transformation suppressor activity (1989) Cell 56: 77–84 (attached hereto as Exhibit 11.
Lin J., et al., Expression of the transformed phenotype induced by diverse acting viral oncogenes mediates sensitivity to growth suppression induced by caffeic acid phenethyl ester (CAPE) (1994) Int'l J. Oncol. 5: 5–15 (attached hereto as Exhibit 12).
Sato, K.Y., et al., Analysis of the tumor suppressor activity of the K–rev–1 gene in human tumor cell lines (1994) Cancer Res. 54: 552–559 (attached hereto as Exhibit 13).
Schneider, C., et al., Genes specifically expressed at growth arrest of mammalian cells (1988) Cell 54: 787–793 (attached hereto as Exhibit 14).
Su Z–z, et al., Defining the critical gene expression changes associated with expression and suppression of the tumorigenic and metastatic phenotype in Ha–ras–transformed cloned rat embryo fibroblast cells (1993) Oncogene 8: 1211–1219 (attached hereto as Exhibit 15).
Su Z–z, et al., Transcriptional switching model for the regulation of tumorigenesis and metastasis by the Ha–ras tumor suppressor gene lysyl oxidase (1995) Int'l J. of Oncol. 7: 1279–1284 (attached hereto as Exhibit 16).
Svinarich, D.M., et al., Charaterization of the human lysyl oxidase gene locus (1992) J. Bio. Chem. 267: 14382–14387 (attached hereto as Exhibit 17).
Velculescu, V.E., et al., Serial analysis of gene expression (1995) Science 270: 484–487 (attached hereto as Exhibit 18).

* cited by examiner

Primary Examiner—Paula K. Hutzell
Assistant Examiner—Geetha P. Bansal
(74) Attorney, Agent, or Firm—John P. White; Cooper & Dunham LLP

(57) ABSTRACT

This invention provides a method for determining whether a compound is capable of suppressing ras functions comprising: (a) contacting an effective amount of the compound with Ha-ras transformed cloned rat embryo fibroblast cells under conditions permitting the compound to suppress ras functions in the cells; and (b) determining the expression or inhibition of certain indicator gene or genes, thereby determining whether the compound is capable of suppressing ras function. This invention further provides the determined compound and a pharmaceutical composition comprising the compound and a pharmaceutically acceptable carrier. This invention also provides methods for generating transcriptional switched Ha-ras transformed cloned rat embryo fibroblast cells. This invention also provides the generated cells and different uses of the cells.

5 Claims, 5 Drawing Sheets

METHODS FOR DETERMINING COMPOUNDS CAPABLE OF INHIBITING THE ACTIVITIES OF THE HA-RAS ONCONGENE

This application claims priority of U.S. provisional application No.60/007,543, filed Nov. 24, 1995, the content of which is incorporated into this application by reference.

The invention disclosed herein was made with Government support under NCI/NIH CA 35675 from the Department of Health and Human Service. Accordingly, the U.S. Government has certain rights in this invention.

BACKGROUND OF THE INVENTION

Throughout this application, various reference are referred to by abbreviation. Disclosures of these publication in their entireties are hereby incorporated by reference into this application to more fully describe the state of the art to which this invention pertains. Full bibliographic citations for these references may be found at the end of this application, preceding the claim.

A model system is described that allows an analysis of the molecular and biochemical changes associated with expression and suppression of the oncogenic and metastatic phenotype of cloned rat embryo fibroblast (CREF) cells. Ha-ras-transformed CREF cells are morphologically transformed, anchorage-independent and both tumorigenic and metastatic in thymic nude mice and syngeneic Fischer rats. Coexpression of the Ha-ras oncogene and Krev-1 tumor suppressor gene in CREF cells results in suppression of in vitro transformation. In contrast, Ha-ras/Krev-1 transformed CREF cells retain, with greatly extended latency periods, both tumorigenic and metastatic capabilities in thymic nude mice. The present study investigates changes in the Ha-ras suppressor gene, rrg (lysyl oxidase), during expression and suppression of the oncogenic phenotype in CREF cells. Nontumorigenic CREF cells and CREF cells transformed by the Ha-ras and Krev-1 gene that express a suppression in in vitro transformation contain elevated levels of lysyl oxidase mRNA and protein. In contrast, Ha-ras and Ha-ras/Krev-1 nude mouse tumor- and nude mouse lung metastasis-derived CREF cells contain reduced levels of lysyl oxidase mRNA and protein. Nuclear run-on assays indicate that suppression of lysyl oxidase expression in transformed subclones of CREF cells correlates with a reduction in transcription of the lysyl oxidase gene. Taken together, the current studies support a transcriptional switching model in which lysyl oxidase expression correlates directly with suppression of the Ha-ras-induced transformation phenotype and escape from oncogenic suppression correlates with a transcriptional silencing of the lysyl oxidase gene and decreased lysyl oxidase mRNA and protein.

Cancer is a multistep process involving a complex interplay between genes that promote the cancer phenotype (oncogenes) and genes that normally function as inhibitors of oncogenesis (tumor suppressor genes) (1–4). A genetic change seen in a high percentage of human cancers is the mutational activation of the cellular ras gene (5,6). The ras gene encodes a 21,000 $M_r$ (ras p21) GTP-binding protein with intrinsic GTPase activity (5–7). In its cellular and mutated forms, ras p21 impinges on a number of signal transduction pathways resulting in growth stimulation, transformation and differentiation (5–9). Over expression of the mutant Ha-ras or Ki-ras oncogene in rodent fibroblasts results in morphological transformation and acquisition of oncogenic potential (5–9). By transfecting a human expression vector cDNA library into a v-Ki-ras-transformed NIH 3T3 cell line (DT), Noda et al (10,11) identified a gene, Krev-1, capable of suppressing the ras-induced transformation phenotype in DT cells. Krev-1 encodes a p21 protein with approximately 50% homology to the ras p21 oncogene-encoded gene product (11). Prominent areas of similarity between Krev-1 p21 and ras p21 are in the functional domains of these proteins, including regions involved in GTP binding and GTPase activity, the isoprenylation signal sequence and the ras/GTPase-activating protein (GAP) effector binding domain (11). Studies using chimeric ras-Krev-1 genes suggest that Krev-1 suppresses ras-induced transformation by directly binding with and sequestering ras p21 effector target molecules necessary for cellular transformation (12–14).

Transfection of a Ha-ras oncogene into cloned rat embryo fibroblast (CREF) cells results in morphological transformation, anchorage-independence and acquisition of tumorigenic and metastatic potential (15,16). Ha-ras-transformed CREF cells exhibit major changes in the transcription and steady-state levels of genes involved in suppression and induction of oncogenesis (15). These include: a reduction in the level of expression of nm23 (a putative metastasis suppressing gene) and TIMP-1 (tissue inhibitor of metalloproteinase-1); and an increase in the levels of cripto, 92-kDa gelatinase/type IV collagenase (92-kDa GEL), osteopontin (OPN) and transin/stomelysin (15). Simultaneous overexpression of Krev-1 in Ha-ras-transformed CREF cells results in morphological reversion, suppression of agar growth capacity and a delay in in vivo oncogenesis (15,16). Reversion of transformation in Ha-ras/Krev-1-transformed CREF cells correlates with a reversion in the transcriptional and steady-state mRNA profile to that of nontransformed CREF cells (15). Following long latency times, Ha-ras/Krev-1 transformed CREF cells form both tumors and metastases in a thymic nude mice (15,16). In the present study, applicants have determined the level of expression of the ras recision gene (rrg, which is lysyl oxidase) (17–19) as a function of expression and suppression of the transformed and oncogenic phenotype. Applicants demonstrate that lysyl oxidase expression (mRNA and protein levels) correlates with suppression of the oncogenic phenotype. As tumors form following escape from Krev-1 induced suppression, both lysyl oxidase and TIMP-1 expression are transcriptionally extinguished. When metastases develop from Krev-1 suppressed CREF cells, both lysyl oxidase and TIMP-1 expression remain suppressed and transcription of the 92-kDa GEL and transin is initiated. These results indicate that transcriptional switching, involving extinction of specific suppressor genes and induction of specific cancer promoting genes, occurs in a defined sequence during expression, suppression and escape from suppression of transformation and oncogenesis.

SUMMARY OF THE INVENTION

This invention provides a method for determining whether a compound is capable of suppressing ras functions comprising: (a) contacting an effective amount of the compound with Ha-ras transformed cloned rat embryo fibroblast cells under conditions permitting the compound to suppress the ras functions in the cells; and (b) determining the expression of lysyl oxidase, the expression of lysyl oxidase indicating that the compound is capable of suppressing the ras function.

This invention also provides a method for determining whether a compound is capable of suppressing the ras functions comprising:(a) contacting an effective amount of the compound with Ha-ras transformed cloned rat embryo fibroblast cells under conditions permitting the compound to suppress the ras functions in the cells; and (b) determining the expression of TIMP-1, the expression of TIMP-1 indicating that the compound is capable of suppressing the ras functions.

This invention also provides a method for determining whether a compound is capable of suppressing the ras functions comprising: (a) contacting an effective amount of the compound with Ha-ras transformed cloned rat embryo fibroblast cells under conditions permitting the compound to suppress the ras functions in the cells; and (b) determining the expression of 92-kDa gelatinase, the inhibition of the expression of 92-kDa gelatinase indicating that the compound is capable of suppressing the ras functions.

This invention also provides a method for determining whether a compound is capable of suppressing ras functions comprising:(a) contacting an effective amount of the compound with Ha-ras transformed cloned rat embryo fibroblast cells under conditions permitting the compound to suppress the ras functions in the cells; and (b) determining the expression of transin, the inhibition of the expression of transin indicating that the compound is capable of suppressing the ras functions.

In an embodiment, the tested compounds were not previously known. This invention also provides compounds which are determined to be capable of suppressing the ras functions by the above methods.

This invention also provides a pharmaceutical composition comprising the compound determined to be capable of suppressing ras functions by the above methods and a pharmaceutically acceptable carrier.

This invention provides a method for generating transcriptional switched Ha-ras transformed cloned rat embryo fibroblast cells comprising: (a) introducing a gene to the Ha-ras transformed cloned rat embryo fibroblast cells; and (b) determining the expression of lysyl oxidase in the introduced cells, the expression of lysyl oxidase indicating that the cells are transcriptional switched.

This invention also provides a method for generating transcriptional switched Ha-ras transformed cloned rat embryo fibroblast cells comprising: (a) introducing a gene to the Ha-ras transformed cloned rat embryo fibroblast cells; and (b) determining the expression of TIMP-1 in the introduced cells, the expression of TIMP-1 indicating that the cells are transcriptional switched.

This invention provides a method for generating transcriptional switched Ha-ras transformed cloned rat embryo fibroblast cells comprising: (a) introducing a gene to the Ha-ras transformed cloned rat embryo fibroblast cells; and (b) determining expression of the 92-kDa gelatinase in the introduced cells, the inhibition of the expression of the 92-kDa gelatinase indicating that the cells are transcriptional switched.

This invention provides a method for generating transcriptional switched Ha-ras transformed cloned rat embryo fibroblast cells comprising: (a) introducing a gene to the Ha-ras transformed cloned rat embryo fibroblast cells; (b) determining expression of the transin in the introduced cells, the inhibition of the expression of the transin indicating that the cells are transcriptional switched.

In an embodiment, the gene is a tumor suppressor gene.

The invention also provides a method to isolated genes which are associated with transcriptional switching of the Ha-ras transformed cloned rat embryo fibroblast cells comprising: (a) selecting genes which are either expressed or suppressed in the transcriptional switched Ha-ras transformed cloned rat embryo fibroblast cells; and (b) isolating the selected gene. This invention also provides genes isolated by the above method. This invention also provides polypeptides encoded by the isolated gene. This invention further provides molecules capable of either competitively inhibiting or mimicking the functions of the polypeptides.

DETAILED DESCRIPTION OF THE INVENTION

Figure 1:
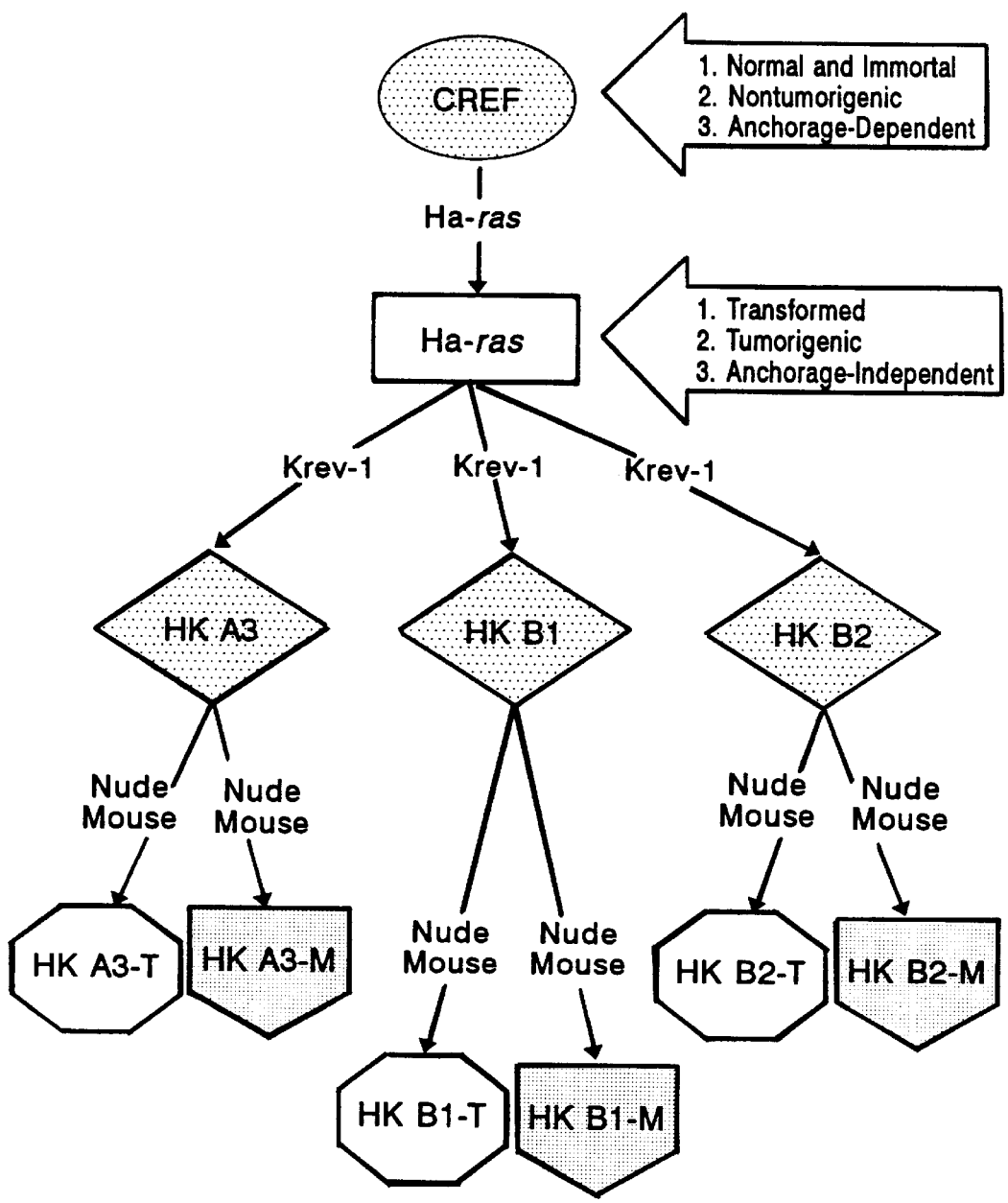
FIG. 1. CREF system used to study induction and suppression of the transformed and oncogenic phenotype. CREF cells are normal and immortal rat embryo fibroblast cells that do not form colonies in agar or induce tumors in nude mice. Transfection of CREF cells with the Ha-ras oncogene, Ha-ras cells, results in morphological transformation, anchorage independence and acquisition of tumorigenic and metastatic properties. Coexpression of Krev-1 in Ha-ras cells, HK A3, HK B1 and HK B2 clones, induces morphological reversion to a CREF-like morphology, a reduction in anchorage independence and a suppression in oncogenicity. Injection of Ha-ras/Krev-1-transformed CREF cells into nude mice results after extended latency periods in tumors (HK A3-T, HK B1-T and HK B2-T clones) and lung metastases (HK A3-M, HK B1-M and HK B2-M clones). Tumor- and metastasis-derived clones reacquire specific transformation related properties.

This invention provides a method for determining whether a compound is capable of suppressing the ras functions comprising: (a) contacting an effective amount of the compound with Ha-ras transformed cloned rat embryo fibroblast cells under conditions permitting the compound to suppress the ras functions in the cells; and (b) determining the expression of lysyl oxidase, the expression of lysyl oxidase indicating that the compound is capable of suppressing the ras functions.

This invention also provides a method for determining whether a compound is capable of suppressing the ras functions comprising:(a) contacting an effective amount of the compound with Ha-ras transformed cloned rat embryo fibroblast cells under conditions permitting the compound to suppress the ras functions in the cells; and (b) determining the expression of TIMP-1, the expression of TIMP-1 indicating that the compound is capable of suppressing the ras functions.

This invention also provides a method for determining whether a compound is capable of suppressing the ras functions comprising: (a) contacting an effective amount of the compound with Ha-ras transformed cloned rat embryo fibroblast cells under conditions permitting the compound to suppress the ras functions in the cells; and (b) determining the expression of 92-kDa gelatinase, the inhibition of the expression of 92-kDa gelatinase indicating that the compound is capable of suppressing the ras function.

This invention also provides a method for determining whether a compound is capable of suppressing the ras functions comprising:(a) contacting an effective amount of the compound with Ha-ras transformed cloned rat embryo fibroblast cells under conditions permitting the compound to suppress the ras functions in the cells; and (b) determining the expression of transin, the inhibition of the expression of transin indicating that the compound is capable of suppressing the ras functions.

In an embodiment, the tested compounds were not previously known. This invention also provides compounds which are determined to be capable of suppressing the ras functions by the above methods.

This invention also provides a pharmaceutical composition comprising the compound determined to be capable of suppressing ras functions by the above methods and a pharmaceutically acceptable carrier.

Pharmaceutically acceptable carriers are well-known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method for generating transcriptional switched Ha-ras transformed cloned rat embryo fibroblast cells comprising: (a) introducing a gene to the Ha-ras transformed cloned rat embryo fibroblast cells; and (b) determining the expression of lysyl oxidase in the introduced cells, the expression of lysyl oxidase indicating that the cells are transcriptional switched.

This invention also provides a method for generating transcriptional switched Ha-ras transformed cloned rat embryo fibroblast cells comprising: (a) introducing a gene to the Ha-ras transformed cloned rat embryo fibroblast cells; and (b) determining the expression of TIMP-1 in the introduced cells, the expression of TIMP-1 indicating that the cells are transcriptional switched.

This invention provides a method for generating transcriptional switched Ha-ras transformed cloned rat embryo fibroblast cells comprising: (a) introducing a gene to the Ha-ras transformed cloned rat embryo fibroblast cells; and (b) determining expression of the 92-kDa gelatinase in the introduced cells, the inhibition of the expression of the 92-kDa gelatinase indicating that the cells are transcriptional switched.

This invention provides a method for generating transcriptional switched Ha-ras transformed cloned rat embryo fibroblast cells comprising: (a) introducing a gene to the Ha-ras transformed cloned rat embryo fibroblast cells; and (b) determining expression of the transin in the introduced cells, the inhibition of the expression of the transin indicating that the cells are transcriptional switched.

This invention also provides the above methods, wherein the gene is a tumor suppressor gene. Tumor suppressor gene are well-known in the art. In an embodiment, the tumor suppressor gene is Krev-1. In another embodiment, the gene may be dominant/negative ras mutant.

This invention also provides cells generated by above methods.

This invention also provides a method to isolated genes which are associated with transcriptional switching of the Ha-ras transformed cloned rat embryo fibroblast cells comprising: (a) selecting genes which are either expressed or suppressed in the transcriptional switched Ha-ras transformed cloned rat embryo fibroblast cells; and (b) isolating the selected gene.

In an embodiment of the above methods, the genes are selected by subtractive hybridization. The technique of subtractive hybridization is well-known in the art (See for example Jiang and Fisher, 1993 and Schneider et al. 1988).

In another embodiment, the genes are selected by differential display. The genes may also be selected by Serial Analysis of Gene Expression (SAGE) (See Velculescu, et al. 1995 for a protocol).

This invention further provides genes isolated by the above method. This invention also provides polypeptides encoded by the isolated gene. This invention further provides molecules capable of either competitively inhibiting or mimicking the functions of the polypeptides.

Once the gene is isolated, the protein encoded by the genes may be determined by decoding the sequences.

This invention will be better understood from the Experimental Detail which follow. However, one skilled in the art will readily appreciate that the specific methods and results discussed are merely illustrative of the invention as described more fully in the claims which follow thereafter.

Experimental Details

Materials and Methods

Cell lines and culture conditions. The CREF cell line is a clonal derivative of the F2408 Fischer rat embryo fibroblast cell line (20). Ha-ras-transformed CREF cells (Ha-ras) were obtained following transfection of CREF cells with the Ha-ras (T24) oncogene and isolating a focus of cells displaying a transformed morphology (21). Ha-ras/Krev-1 cells, containing the Ha-ras and Krev-1 gene, were obtained by cotransfecting Ha-ras cells with a hygromycin resistance gene (pRSV1.1) and selecting cells resistant to hygromycin and displaying a reversion in morphology to that of non-transformed CREF cells (15). For the present study, three independent Ha-ras/Krev-1 clonal isolates, HK B1, HK B2 and HK A3, were used (15). Additionally, nude-mouse tumor-derived clones (HK B1-T and HK B2-T) and lung metastasis-derived clones (HK B1-M, HK B2-M and HK A3-M) were studied (15). All cell lines were grown in Dulbecco's modified Eagle's medium containing 5% fetal bovine serum in a 5% $CO_2$- 95% air-humidified incubator.

Nucleic acid analysis. In vitro transcription within isolated nuclei was performed as previously described (22). Nuclei from approximately $2 \times 10^6$ cells were isolated and RNA previously initiated by RNA polymerase II were allowed to elongate in the presence of [$^{32}$P]UTP. Nuclear RNA was isolated, purified by filtering through a G-50 Sephadex column. Nuclear RNA was extracted, purified by filtering onto Millipore (0.45-mm) filters followed by elution and denaturing by treatment with 0.1 M sodium hydroxide for 5 min on ice. Nylon membranes containing 2 μg of the appropriate denatured plasmid DNA gene insert were hybridized with [$^{32}$P]-labeled RNA from the different cell types as previously described (15,22). Steady-state mRNA levels were determined by Northern blotting using appropriate multiprime [$^{32}$P]-labeled DNA probes as described by Su et al (15,16).

Western blotting analysis. Western blotting analysis was performed as described previously (23). Cell lysates were prepared from logarithmical growing cells in 50 mM Tris (pH 8.0), 150 mM NaCl, 0.02% NaN3, 100 mg/ml PMSF (phenylmethylsulfonyl fluoride), 1 mg/ml aprotinin and 1% NP40 (24), and protein concentrations were determined using the Bio-Rad protein assay (25). One hundred μg of cell lysates were separated on 10% SDS-PAGE under reducing conditions (26) and transferred to a 0.45 mm nitrocellulose membrane (27). The membranes were blocked in TBS (10 mM NaCl, pH 7.5) containing 1% BSA for 1 hr at room temperature. The membrane was then incubated with lysyl oxidase antiserum made in rabbits (1:500 in TBS-1% BSA) (28) or actin monoclonal antibody (Oncogene Sciences) for 2 hr at room temperature, washed 3× with TBS and incubated with peroxidase labeled goat anti-rabbit IgG (H+L) (GIBCO-BRL, NY). Finally the membrane was washed 3× with TBS and color was developed using diaminobenzidine as the substrate (29). Lysyl oxidase antibodies produced against the purified 32-kDa bovine aortic enzyme were kindly supplied by Dr. H. M. Kagan (28).

Experimental Results

Previous studies demonstrate that Krev-1 suppression of Ha-ras induced oncogenesis in transformed CREF cells does not persist when doubly-transformed cells are injected into nude mice (15). Ultimately, both tumors and lung metastases develop in nude mice subcutaneously injected with in vitro transformation-suppressed Ha-ras/Krev-1 cells (15). A schematic representation of this process is shown in FIG. 1. Escape from oncogenic suppression requires long latency times after subcutaneous injection of doubly transformed cells (15), and in many ways mimic's cancer development in humans. In contrast, injection of Ha-ras/Krev-1 cells into the bloodstream of nude mice, i.e., experimental metastasis assay, does not result in lung metastases (15). By reestablishing both tumor- and metastases-derived Ha-ras/Krev-1 cells in culture, a model system is now available to determine the gene expression changes associated with a normal cellular phenotype (CREF), a tumorigenic and metastatic phenotype (Ha-ras), a suppressed transformed phenotype (Ha-ras/Krev-1: HK), acquisition of a tumorigenic phenotype (Ha-ras/Krev-1 T: HK B1-T and HK B2-T) and acquisition of a metastatic phenotype (Ha-ras/Krev-1 M: HK A3-M, HK B1-M and HK B2-M) (FIG. 1). These stable cell types were used to investigate changes in expression of the putative ras suppressor gene rrg (lysyl oxidase) (17–19) in expression and suppression of the transformed and oncogenic phenotype.

Figure 2:
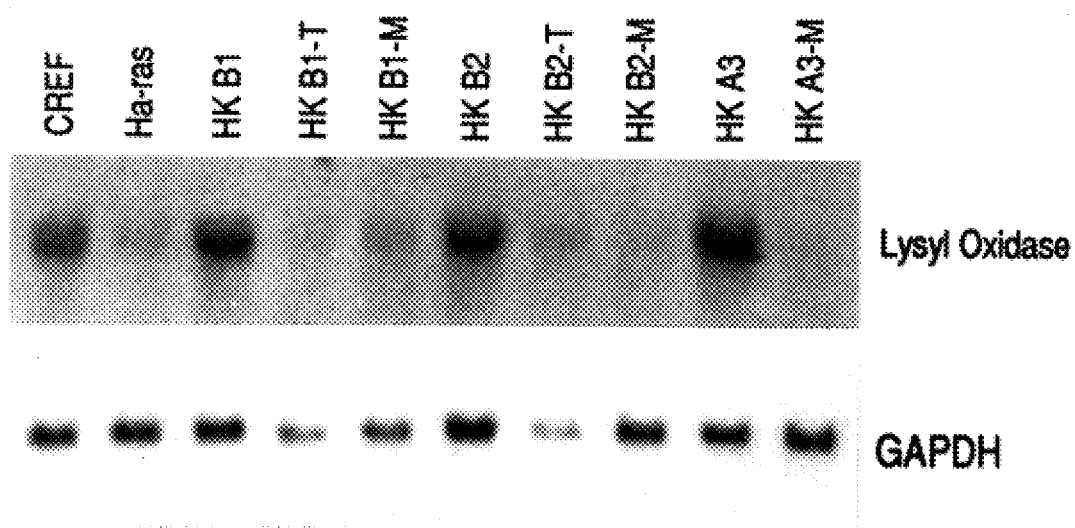
FIG. 2. Northern blotting analysis of steady-state lysyl oxidase and GAPDH mRNAs in CREF and Ha-ras- and Ha-ras+Krev-1-transformed CREF clones. A 15-μg aliquot of total cellular RNA was run on a 1.0% agarose gel and transferred to a nylon membrane. Blots were hybridized with a multiprime [$^{32}$P]-labeled lysyl oxidase gene probe. Filters were stripped and rehybridized with a multiprime [$^{32}$P]-labeled GAPDH gene probe.
Figure 3:
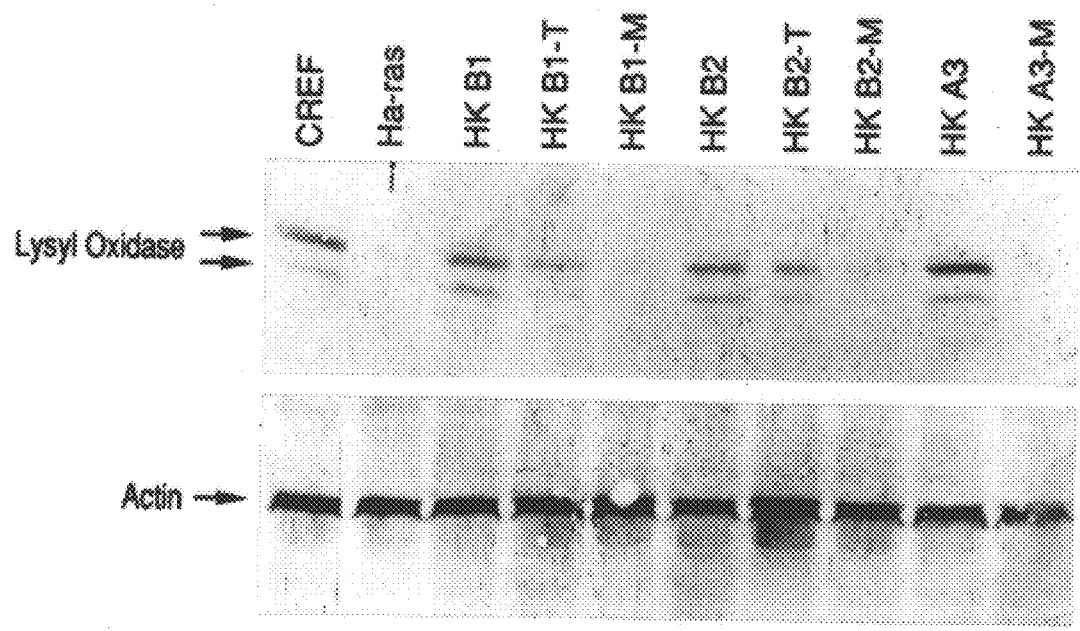
FIG. 3. Western blotting analysis of lysyl oxidase and actin protein in CREF and Ha-ras and Ha-ras+Krev-1-transformed CREF clones. A 100-μg aliquot of cell lysate prepared from logarithmically growing cells was separated by electrophoresis on a 10% SDS polyacrylamide gel, transferred to a nitrocellulose membrane, incubated with lysyl oxidase antiserum or actin monoclonal antibody followed by incubation with peroxidase-labeled goat anti-rabbit IgG and color was developed with diaminobenzidine as a substrate.

Northern blotting analysis was used to determine the relative levels of lysyl oxidase and GAPDH RNA in CREF, Ha-ras, Ha-ras/Krev-1 (HK B1, HK B2 and HK A3), Ha-ras/Krev-1 nude mouse tumor (HK B1-T and HK B2-T) and Ha-ras/Krev-1 nude mouse lung metastasis (HK B1-M, HK B2-M and HK A3-M) clones (FIG. 2). Elevated levels of lysyl oxidase RNA occur in CREF and the three Ha-ras/Krev-1 clones relative to Ha-ras and tumor-derived and metastasis-derived Ha-ras/Krev-1 clones. The relative amount of lysyl oxidase RNA, corrected for GAPDH expression, indicates that CREF, HK B1, HK B2 and HK A3>HK B1-T and HK B2-T>HK B1-M, HK B2-M and HK A3-M cells. Western blotting of total cellular lysates indicates that CREF, HK B1, HK B2 and HK A3 cells contain greater amounts of the anticipated ~46 and ~50 kDa intracellular lysyl oxidase precursor proteins (including lysyl oxidase and its glycosylated form) than Ha-ras and the tumor- and metastasis-derived HK clones (FIG. 3). In the HK metastasis derived clones, no lysyl oxidase protein was detected, whereas tumor-derived HK clones contained lysyl oxidase precursor proteins (FIG. 3). However, the amount of lysyl oxidase precursor proteins in the HK T clones was less than in the parental HK clones. These results indicate that the relative levels of lysyl oxidase protein correlate with the levels of lysyl oxidase RNA (FIGS. 2 and 3). These findings confirm that elevated lysyl oxidase (rrg) expression corresponds to suppression of the oncogenic phenotype, whereas reduced lysyl oxidase expression is a property of oncogenic, both tumorigenic and metastatic, variants of CREF cells.

Figure 4:
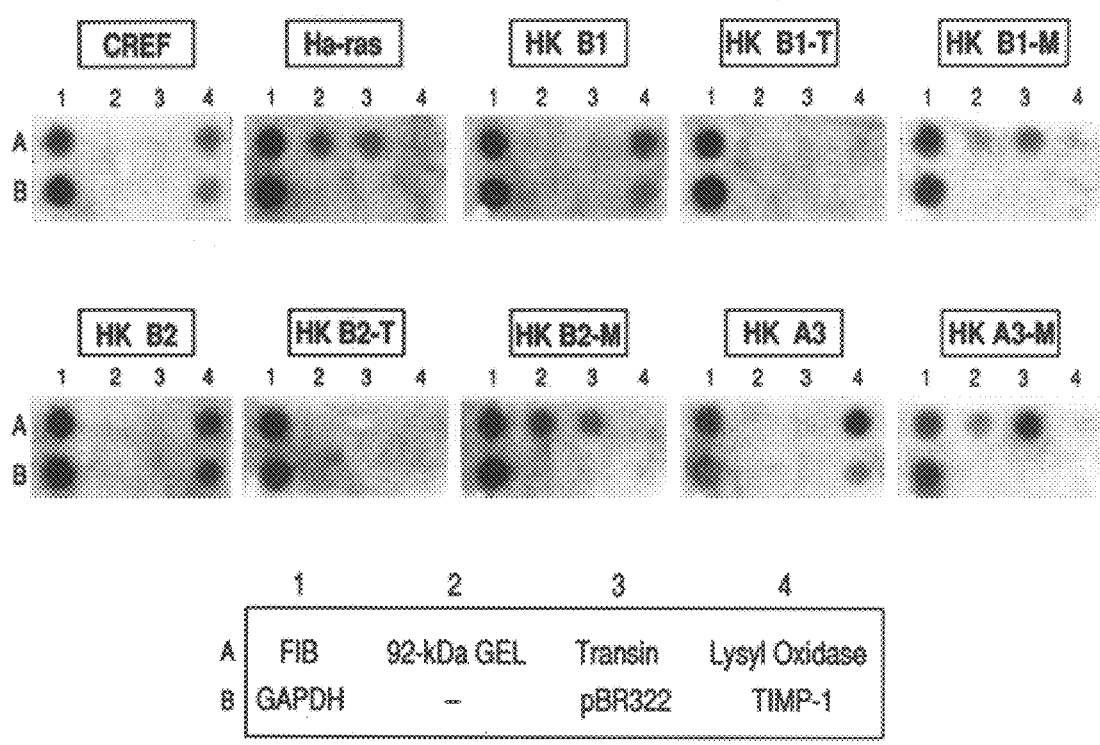
FIG. 4. Analysis of cellular gene transcription rates in CREF and Ha-ras and Ha-ras+Krev-1-transformed CREF clones. Nuclei from 2×10$^6$ cells were isolated from each of the cell lines shown and nuclear RNA was labeled in vitro and subsequently hybridized to denatured DNA probes on nitrocellulose filters. For each hybridization reaction, an equal number of total counts representing a similar number of cell nuclei was used, so that comparative rates of transcription could be obtained. Cell line designation: CREF, cloned rat embryo fibroblast cell line, Ha-ras, T24 (Ha-ras)-transformed CREF clone, HK A3, HK B1 and HK B2, Ha-ras clones transfected with the Krev-1 gene. T, tumor derived; M, metastasis derived. The gene probes utilized are shown in the order presented in the box and they include: fibronectin (FIB); 92-kDa gelatinase/type IV collagenase (92-kDa GEL); transin (stromelysin); lysyl oxidase (rrg); glyceraldehyde phosphate dehydrogenase (GAPDH);—(no probe); pBR322; and tissue inhibitor of metalloproteinase 1 (TIMP-1).
Figure 5:
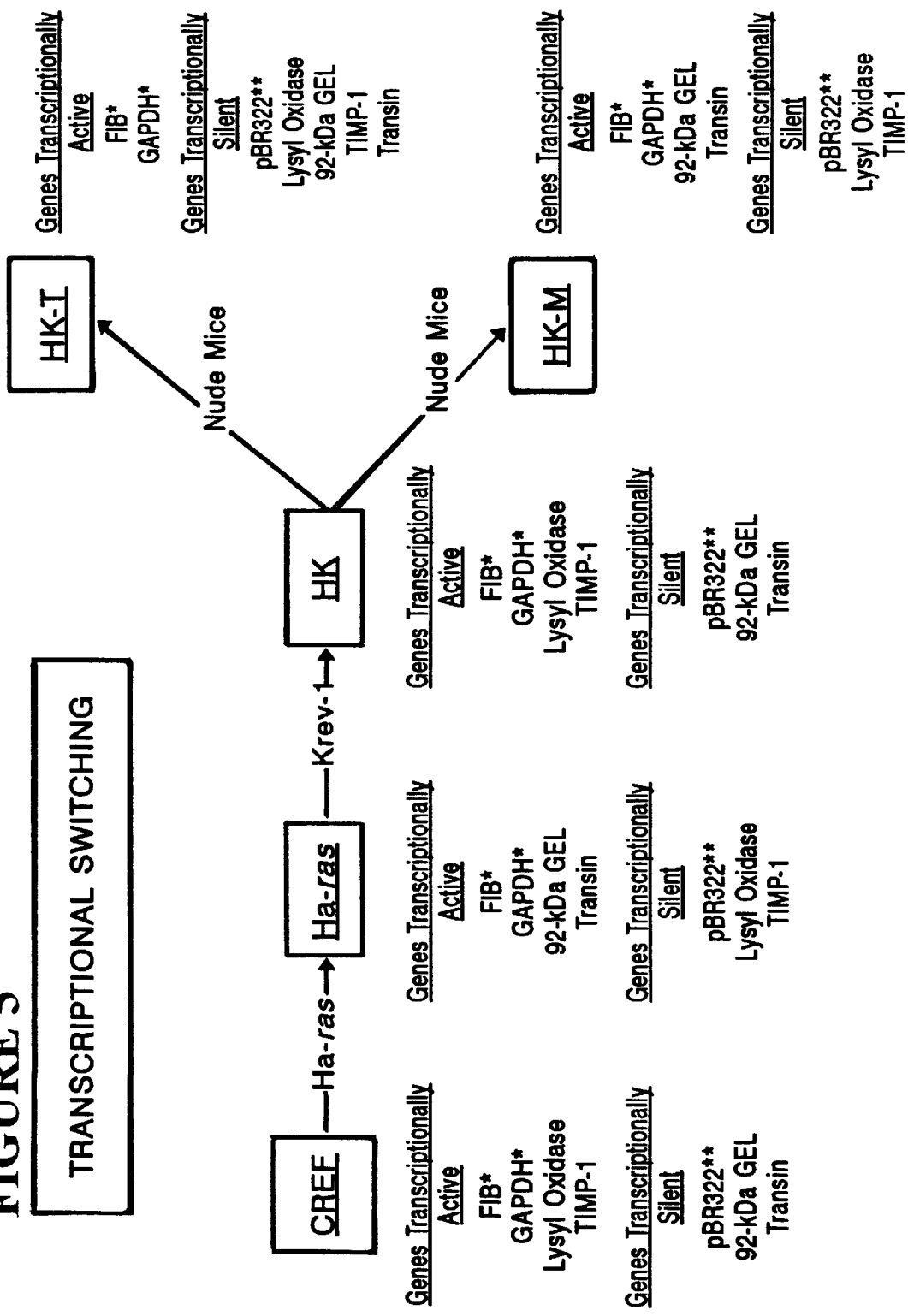
FIG. 5. Transcriptional switching model for induction, suppression and escape from suppression of oncogenicity in Ha-ras-transformed CREF cells. Genes actively transcribed in CREF, Ha-ras, HK, HK-T and HK-M cells include fibronectin (FIB*) and glyceraldehyde phosphate dehydrogenase (GAPDH*). Genes not transcribed in CREF, Ha-ras, HK, HK-T and HK-M cells include plasmid DNA (pBR322**). Transcriptional switching involves the selective transcriptional silencing of genes normally expressed in CREF cells, such as lysyl oxidase and TIMP-1, and the transcriptional activation of genes normally not expressed in CREF cells, such as 92-kDa GEL and transin (stromelysin), following transformation by Ha-ras. Suppression of the transformed phenotype by Krev-1 results in a transcriptional reversion of Ha-ras-transformed cells to a CREF-like transcriptional profile. Escape from transformation suppression following tumor formation in nude mice by Ha-ras plus Krev-1 transformed CREF cells results in decrease transcription or the transcriptional silencing of the tumor suppressor genes lysyl oxidase and TIMP-1, respectively. Formation of metastases correlates with the continuous suppression of the tumor suppressor genes lysyl oxidase and TIMP-1 and the concurrent transcriptional activation of progression promoting genes encoding 92-kDa GEL and transin (stromelysin). The transcriptional profile of metastasis-derived HK cells is identical to that of the Ha-ras-transformed parental cells.

Previous studies document a specific pattern of gene transcription of oncogenic suppressing (nm23-H1 and TIMP-1) and oncogenic promoting (92-kDa GEL, osteopontin, cripto and transin/stromelysin) genes in the same panel of cells used for the present studies (14). To determine if the regulation of lysyl oxidase expression occurs at a transcriptional level, nuclear run-on assays were performed (FIG. 4). CREF cells contain RNA transcripts for two positive expressing genes, fibronectin (FIB) and GAPDH, and the two suppressor genes, TIMP-1 and lysyl oxidase. In contrast, no transcripts are detected for the 92-kDa GEL, transin or the negative control (pBR322). Ha-ras cells display a different transcriptional profile, i.e., they express FIB, GAPDH, 92-kDa GEL and transin, but not lysyl oxidase or TIMP-1. Coexpression of Ha-ras and Krev-1 in CREF cells results in the same transcriptional profile as seen in CREF cells (FIG. 4). During escape from transformation suppression, a defined pattern of transcriptional switching is observed. In tumor-derived Ha-ras/Krev-1 cultures RNA transcripts for both lysyl oxidase and TIMP-1 are no longer apparent. However, on the basis of Western blotting data, some transcription may still be occurring, because lysyl oxidase precursor proteins are detected in HK B1-T and HK B2-T cells. In metastasis-derived Ha-ras/Krev-1 clones a return to the transcriptional pattern of Ha-ras cells is observed, i.e., both lysyl oxidase and TIMP-1 are not expressed and both the 92-kDa GEL and transln are expressed (FIG. 4). These results indicate that transcriptional switching occurs in a defined sequence during escape from transformation suppression in vivo (FIG. 5). First, specific tumor suppressor genes become transcriptionally silenced during acquisition of tumorigenic potential. Second, tumor cells reexpress specific cancer promoting genes resulting in acquisition of metastatic potential.

Experimental Discussion

Applicants presently demonstrate that acquisition of a tumorigenic and metastatic phenotype by Ha-ras/Krev-1 in vitro suppressed CREF cells involves a temporal alteration in the transcription of specific target genes (FIG. 5). These changes include an initial loss (or reduction) of suppressor gene transcription associated with escape from tumorigenic suppression and then a transcriptional activation of genes directly correlated with the capacity to induce metastases. A component of this transcriptional reprogramming is the ras suppressor gene rrg (lysyl oxidase), an important enzyme in extracellular matrix formation (28) (FIG. 4). Changes in lysyl oxidase transcription in the CREF system are also associated with corresponding modifications in the levels of lysyl oxidase mRNA and protein (FIGS. 2 and 3). Using subtraction hybridization between mRNA from preneoplastic rat 208F fibroblasts and a Ha-ras-transformed 208F subclone, a lysyl oxidase cDNA has been isolated based on its decreased expression in Ha-ras transformed cells (30). In the 208F fibroblast system the level of lysyl oxidase mRNA correlates with suppression in anchorage independence rather than presence of a flat morphology characteristic of the normal cellular phenotype (30). In the CREF system, acquisition of tumorigenic and metastatic properties by Ha-ras/Krev-1 cells corresponds with down-regulation of lysyl oxidase and a more transformed morphology in comparison with CREF and Ha-ras/Krev-1 in vitro suppressed cells. Tumor- and metastasis-derived Ha-ras/Krev-1 cells also grow with increased efficiency in agar in comparison with Ha-ras/Krev-1 in vitro suppressed cells, but anchorage-independence never achieves that of parental Ha-ras transformants (15). Transfection of a non-small-cell lung carcinoma cell line, Calu-6, that contains an activated Ki-ras oncogene with Krev-1 results in transfectants that display a more differentiated squamous epithelial morphology and a reduction in tumorigenicity (31). Similarly, experiments by Kitayama et al (13) indicate that transfection of Krev-1 into the human tumor cell line HT1080, that contains an N-ras oncogene, also results in a suppression in the transformed phenotype and tumorigenicity. Recent studies by Sato et al (32) have explored the relationship between forced expression of the Krev-1 gene and the transformation and tumorigenic properties of several human tumor cells containing activated ras oncogenes. Using both epitope-tagged wild-type and activated mutant K-rev-1 complementary expression vectors, no significant effect on morphology, in vitro growth or tumorigenicity was apparent. Since the human tumor cells analyzed, including the HT1080 sublime, EJ and SW480, may have accumulated numerous genetic changes, it is possible that the absence of an effect of Krev-1 in these cells is a consequence of its inability to suppress those additional genetic alterations. Alternatively, forced expression of Krev-1 may correlate with suppression in specific transformation pathways, some of which may be cell type or even subclone specific.

Transcriptional switching is associated with the selective suppression of a number of putative tumor and metastasis suppressor genes, lysyl oxidase, TIMP-1 and nm23, and the activation of several cancer promoting genes, osteopontin, 92-kDa GEL, cripto and transin. In contrast, expression of additional tumor suppressor, such as the retinoblastoma gene and the p53 gene, and cancer related genes, such as fibronectin, 72-kDa GEL and tenascin, are not altered transcriptionally as a function of transformation suppression or escape from transformation suppression (15). These observations make it difficult to assign a specific contribution of each of the gene expression changes in these processes. For example, applicants do not know the order of suppressor gene inactivation during escape from oncogenic suppression or if inactivation of a single suppressor gene will promote tumorigenic conversion. Similarly, the order of activation of the cancer promoting genes or whether a single or multiple genes can function to facilitate acquisition of metastatic competence remains to be determined. One approach to address these questions is to selectively express (sense expression constructs) or selectively inhibit (antisense expression constructs) specific genes separately and in combination and evaluate the effect on transcription of additional genes and expression of transformation related phenotypes. In the case of lysyl oxidase, introduction of an antisense oriented expression construct containing a partial mouse lysyl oxidase cDNA effectively downregulates lysyl oxidase mRNA and induces a transformed phenotype in LTR-c-Ha-ras transformed mouse NIH 3T3 cells (17). Experiments to determine if a similar construct can induce a transformed phenotype in Ha-ras/Krev-1 in vitro suppressed cells are presently in progress. These types of studies, although laborious, should provide important information relative to the role of specific transcriptional changes in mediating ras and Krev-1 functions.

The mechanism underlying transcriptional switching during escape from tumor and metastasis suppression in Ha-ras/Krev-1 cells is not known. The present study raises a number of intriguing questions relative to this process and the mechanism by which Krev-1 functions as a suppressor of Ha-ras-induced gene expression changes. A proposed hypothesis for Krev-1 suppression of ras is that the Krev-1 protein binds to ras p21 effectors and sequesters these factors thereby attenuating oncogenic ras p21 activity (14,32,33).

The studies by Sato et al (32) using epitope-tagged wild-type Krev-1 proteins provide direct evidence that the Krev-1 protein is localized to the medial/trans-Golgi network. It is possible that the loss of suppression of the transformed phenotype by Ha-ras/Krev-1 transformed CREF cells, without the loss of Krev-1 expression (15), may result because the Krev-1 protein can no longer sequester sufficient quantities of the ras p21 effector molecules. Alternatively, during selection for tumor formation and metastases in nude mice novel genes may become activated that can override Krev-1-induced inhibition of ras activity and induce transcriptional switching. In this context, identification of the gene(s) that may mediate transcriptional switching could provide important insights into the mechanism by which ras functions in signal transduction and as an oncogene. The process of transcriptional switching would also appear amenable for identifying compounds capable of inhibiting farnesyl transferase that is important for insertion of ras p21 into the inner surface of the plasma membrane and critical for ras-induced transformation (7–9).

References

1. Fisher P B: Enhancement of viral transformation and expression of the transformed phenotype by tumor promoters. In Slaga T J, ed. Tumor Promotion and Cocarcinogenesis In Vitro, Mechanisms of Tumor Promotion. Boca Raton Fla., USA: CRC Press, Inc. pp. 57–123, 1984.
2. Bishop J M: Molecular themes in oncogenesis. Cell 64: 235–248, 1991.
3. Liotta L A, Steeg P G, Stetler-Stevenson W G: Cancer metastasis and angiogenesis: an imbalance of positive and negative regulation. Cell 64: 327–336, 1991.
4. Knudson A G: Antioncogenes and human cancer. Proc Natl Acad Sci USA 90: 10914–10921, 1991.
5. Barbacid M: ras genes. Annu Rev Biochem 56: 779–827, 1987.
6. Bos J: ras oncogene in human cancer. Cancer Res 49: 4682–4689, 1989.
7. Grunicke H H, Maly K: Role of GTPases and GTPase regulatory proteins in oncogenesis. Crit Rev Oncogenesis 4 (4): 389–402, 1993.
8. Satoh T, Kaziro Y: Ras in signal transduction. Sem Cancer Biol 3: 169–177, 1992.
9. Khosravi-Far R, Der C J: The Ras signal transduction pathway. Cancer Metastasis Rev 13: 67–89, 1994.
10. Noda M, Kitayama H, Matsuzaki T, Sugimoto Y, Okayama H, Bassin R H, Ikawa Y: Detection of genes with a potential for suppressing the transformed phenotype associated with activated ras genes. Proc Natl Acad Sci USA 86: 162–166, 1988.
11. Kitayama H, Sugimoto Y, Masuzaki T, Ikawa Y, Noda M: A ras-related gene with transformation suppressor activity. Cell 56: 77–84, 1989.
12. Zhang K, Noda M, Vass W, Papageorge A G, Lowy D R: Identification of small clusters of divergent amino acids that mediate the opposing effects of ras and Krev-1. Science (Washington D.C.) 249: 162–165, 1990.
13. Kitayama H, Matsuzaki T, Ikawa Y, Noda M: Genetic analysis of the Kirsten-ras-revertant 1 gene: potentiation of its tumor suppressor activity by specific point mutations. Proc Natl Acad Sci USA 87: 4284–4288, 1990.
14. Frech M, John J, Pizon V, Chardin P, Tavitian A, Clark R, McCormick F, Wittinghofer A: Inhibition of GTPase activating protein stimulation of Ras-p21GTPase by the Krev-1 gene product. Science (Washington D.C.) 249: 169–171, 1990.
15. Su Z-z, Austin V N, Zimmer S G, Fisher P B: Defining the critical gene expression changes associated with expression and suppression of the tumorigenic and metastatic phenotype in Ha-ras-transformed cloned rat embryo fibroblast cells. Oncogene 8: 1211–1219, 1993.
16. Lin J, Su Z-z, Grunberger D, Zimmer S G, Fisher P B: Expression of the transformed phenotype induced by diverse acting viral oncogenes mediates sensitivity to growth suppression induced by caffeic acid phenethyl ester (CAPE). Intl J Oncol 5: 5–15, 1994.
17. Contente S, Kenyon K, Rimoldi D, Friedman R M: Expression of the gene rrg is associated with reversion of NIH 3T3 transformed by LTR-c-H-ras. Science 249:796–798, 1990.
18. Kenyon K, Contente S, Trackman P C, Tang J, Kagan H M, Friedman R M: Lysyl oxidase and rrg messenger RNA. Science 253: 802, 1990.
19. Kenyon K, Modi W S, Contente S, Friedman R M: A novel human cDNA with a predicted protein similar to lysyl oxidase maps to chromosome 15q24-q25. J. Biol Chem 268: 18435–18437, 1993.
20. Fisher P B, Babiss L E, Weinstein I B, Ginsberg H S: Analysis of type 5 adenovirus transformation with a cloned rat embryo cell line (CREF). Proc Natl Acad Sci USA 79: 3527–3531, 1982.
21. Boylon J F, Shih T Y, Fisher P B, Zimmer S G: Induction and progression of the transformed phenotype in cloned rat embryo fibroblast cells: studies employing type 5 adenovirus and wild-type and mutant Ha-ras oncogenes. Mol Carcinog 5: 118–128, 1992.
22. Jiang H, Waxman S, Fisher P B: Regulation of c-fos, c-jun and jun-B gene expression in human melanoma cells induced to terminally differentiate. Mol Cell Different 1 (2): 197–214, 1993.
23. Yemul S, Leon J A, Pozniakoff T, Esser P D, Estabrook A. Radioimmunoimaging of human breast carcinoma xenografts in nude mouse model with $^{111}$In-labeled new monoclonal antibody EBA-1 and F(ab')$_2$ fragments. Nucl Med Biol 20 (3): 325–335, 1993.
24. Sambrook J, Fritsch E F, Maniatis T (Eds) : *Molecular Cloning: A Laboratory Manual*, 2nd edition, Cold Spring Harbor Laboratory Press, New York, 1989.
25. Bradford M: A rapid and sensitive method for the quantitation of microgram quantities of protein utilizing the principle of protein-dye binding. Anal Biochem 72: 248–254, 1976.
26. Laemmli U K: Cleavage of structural proteins during the assembly of the head of bacteriophage T4. Nature 227: 680–685, 1970.
27. Towbin H, Stachlin T, Gordon J: Electrophoretic transfer of proteins from polyacrylamide gels to nitrocellulose sheets: procedure and some applications. Proc Natl Acad Sci USA 76: 4350–4354, 1979.
28. Kagan H M, Trackman P C: Properties and function of lysyl oxidase. Am J Respir Cell Mol Biol 5: 206–210, 1991.
29. Graham R C, Karnovsky M J: The early stages of absorption of injected horseradish peroxidase in the proximal tubules of mouse kidney: ultrastructural cytochemistry by a new technique. J Histochem Cytochem 14: 291–302, 1966.
30. Hajnal A, Klemenz R, Schafer R: Up-regulation of lysyl oxidase in spontaneous revertants of H-ras-transformed rat fibroblasts. Cancer Res 53: 4670–4675, 1993.
31. Caamano J, DiRado M, Iizasa T, Momiki S, Fernandes E, Ashendel C, Noda M, Klein-Szanto A J P: Partial suppression of tumorigenicity in a human lung cancer cell line transfected with Krev-1. Mol Carcinog 6: 252–259, 1992.

32. Sato K Y, Polakis P G, Haubruck H, Fasching C L, McCormick F, Stanbridge E J: Analysis of the tumor suppressor activity of the K-rev-1 gene in human tumor cell lines. Cancer Res 54: 552–559, 1994.
33. Beranger F, Goud B, Tavitian A, de Gunzburg J: Association of the Ras-antagonistic Rap1/Krev-1 proteins with the Golgi complex. Proc Natl Acad Sci USA 88: 1606–1610, 1991.
34. Jiang H, and Fisher P B, Use of a sensitive and efficient subtraction hybridization protocol for the identification of genes differentially regulated during the induction of differentiation in human melanoma cells. Mol. Cell. Different., 1 (3): 285–299, 1993.
35. Schneider C, King R M, and Philipson L Genese specifically expressed at growth arrest of mammalian cells, Cell, 54:787–793 (1988).
36. Velculescu V E, Zhang L, Vogelstein B, and Kinzlex K W, "Serial Analysis of Gene Expression. Science 270: 484–87, 1995.

What is claimed is:

1. A method for determining whether a compound is capable of suppressing the ras transformation phenotype comprising:
   (a) contacting the compound with Ha-ras transformed cloned rat embryo fibroblast cells under conditions permitting the compound to suppress the ras transformation phenotype in the cells; and
   (b) determining the expression of lysyl oxidase, the expression of lysyl oxidase indicating that the compound is capable of suppressing the ras transformation phenotype.

2. A method for determining whether a compound is capable of suppressing the ras transformation phenotype comprising:
   (a) contacting the compound with Ha-ras transformed cloned rat embryo fibroblast cells under conditions permitting the compound to suppress the ras transformation phenotype in the cells; and
   (b) determining the expression of TIMP-1, the expression of TIMP-1 indicating that the compound is capable of suppressing the ras transformation phenotype.

3. A method for determining whether a compound is capable of suppressing the ras transformation phenotype comprising:
   (a) contacting the compound with Ha-ras transformed cloned rat embryo fibroblast cells under conditions permitting the compound to suppress the ras transformation phenotype in the cells; and
   (b) determining the expression of 92-kDa gelatinase, the inhibition of the expression of 92-kDa gelatinase indicating that the compound is capable of suppressing the ras transformation phenotype.

4. A method for determining whether a compound is capable of suppresing the ras transformation phenotype comprising:
   (a) contacting the compound with Ha-ras transformed cloned rat embryo fibroblast cells under conditions permitting the compound to suppress the ras transformation phenotype in the cells; and
   (b) determining the expression of transin, the inhibition of the expression of transin indicating that the compound is capable of suppressing the ras transformation phenotype.

5. A method of claim 1, 2, 3 or 4, where the compound was not previously known.

* * * * *